United States Patent
Westermann et al.

(10) Patent No.: US 10,178,952 B2
(45) Date of Patent: Jan. 15, 2019

(54) BI-HEMISPHERIC BRAIN WAVE SYSTEM AND METHOD OF PERFORMING BI-HEMISPHERICAL BRAIN WAVE MEASUREMENTS

(71) Applicant: WIDEX A/S, Lynge (DK)

(72) Inventors: Soren Erik Westermann, Humlebak (DK); Preben Kidmose, Maarslet (DK); Mike Lind Rank, Farum (DK); Michael Ungstrup, Allerod (DK)

(73) Assignee: Widex A/S, Lynge (DK)

( * ) Notice: Subject to any disclaimer, the term of this patent is extended or adjusted under 35 U.S.C. 154(b) by 1250 days.

(21) Appl. No.: 13/838,351

(22) Filed: Mar. 15, 2013

(65) Prior Publication Data

US 2013/0184552 A1 Jul. 18, 2013

Related U.S. Application Data

(63) Continuation-in-part of application No. PCT/EP2011/050348, filed on Jan. 12, 2011.

(51) Int. Cl.
*A61B 5/0478* (2006.01)
*A61B 5/00* (2006.01)
*A61B 5/0484* (2006.01)

(52) U.S. Cl.
CPC ........ *A61B 5/0006* (2013.01); *A61B 5/04845* (2013.01); *A61B 5/6817* (2013.01); *A61B 5/7264* (2013.01)

(58) Field of Classification Search
None
See application file for complete search history.

(56) References Cited

U.S. PATENT DOCUMENTS

| 6,572,542 B1 * | 6/2003 | Houben ............... A61B 5/0472 128/920 |
| 7,769,439 B2 | 8/2010 | Vesely et al. |
| 2004/0122303 A1 * | 6/2004 | Kopke ............... A61B 5/04845 600/383 |
| 2005/0043774 A1 * | 2/2005 | Devlin ................ A61B 5/048 607/45 |

(Continued)

FOREIGN PATENT DOCUMENTS

| EP | 1238629 A1 | 9/2002 |
| WO | 2006/047874 A1 | 5/2006 |

(Continued)

OTHER PUBLICATIONS

Sackellares, J. Chris. "Seizure prediction and monitoring." Epilepsy & behavior: E&B 18.1-2 (2010): 106.*

(Continued)

*Primary Examiner* — Jacqueline Cheng
*Assistant Examiner* — Jairo Portillo
(74) *Attorney, Agent, or Firm* — Sughrue Mion, PLLC

(57) ABSTRACT

A system (100) for bi-hemispheric brain wave measurements including a first device (102) and a second device (103), wherein at least said first device (102) is adapted to be worn in or at a first ear of a person subject to the measurements and wherein the first (102) and second (103) device exchange data using a wireless link (104). The invention also provides a method for measuring a bi-hemispherical brain wave signal.

27 Claims, 7 Drawing Sheets

(56) References Cited

U.S. PATENT DOCUMENTS

| | | |
|---|---|---|
| 2005/0149144 A1* | 7/2005 | Siever .................. A61M 21/00 607/45 |
| 2006/0025648 A1* | 2/2006 | Lupin .................. H04R 25/606 600/25 |
| 2006/0094974 A1 | 5/2006 | Cain |
| 2006/0217632 A1* | 9/2006 | Causevic ............. A61B 5/0482 600/559 |
| 2007/0112277 A1 | 5/2007 | Fischer et al. |
| 2007/0133832 A1* | 6/2007 | DiGiovanni ......... H04R 25/552 381/320 |
| 2007/0282216 A1 | 12/2007 | Vesely |
| 2008/0183096 A1* | 7/2008 | Snyder ................ G06K 9/00496 600/545 |
| 2009/0124923 A1* | 5/2009 | Sackellares ............ A61B 5/048 600/544 |
| 2009/0163828 A1 | 6/2009 | Turner et al. |
| 2010/0280338 A1* | 11/2010 | Chou .................. A61B 5/6838 600/301 |

FOREIGN PATENT DOCUMENTS

| | | |
|---|---|---|
| WO | 2007/150003 A2 | 12/2007 |
| WO | 2010/115451 A1 | 10/2010 |
| WO | 2010/149157 A1 | 12/2010 |
| WO | 2011/000375 A1 | 1/2011 |
| WO | 2011/006681 A1 | 1/2011 |
| WO | 2011/124251 A | 10/2011 |

OTHER PUBLICATIONS

International Search Report and Written Opinion for PCT/EP2011/050348.

* cited by examiner

BI-HEMISPHERIC BRAIN WAVE SYSTEM AND METHOD OF PERFORMING BI-HEMISPHERICAL BRAIN WAVE MEASUREMENTS

RELATED APPLICATIONS

The present application is a continuation-in-part of application PCT/EP2011050348, filed on 12 Jan. 2011, in Europe, and published as WO2012095171 A1.

BACKGROUND OF THE INVENTION

1. Field of the Invention

The present invention relates to brain wave measurement. The invention further relates to a system for performing bi-hemispherical brain wave measurements. More specifically the invention relates to a system for performing bi-hemispherical brain wave measurements where at least a part of the system is adapted to be worn in or at an ear of a person subject to the measurements. Moreover the invention relates to a method for performing bi-hemispherical brain wave measurements.

It is generally known, particularly within medical science, to measure brain waves by placing electrodes on the scalp of a subject whose brain waves it is desired to measure (for simplicity denoted "subject" in the following), and to view, process and interpret the measured brain waves using suitable equipment. Typically, such equipment is an electroencephalograph, by means of which a so-called electroencephalogram (EEG) may be achieved. An electroencephalograph provides a measurement and a recording of electrical activity in a subject's brain by measuring the electric potential generated on the surface of the subject's scalp by currents flowing between synapses in the subject's brain. Within medical science brain waves are used for various diagnostic purposes.

2. The Prior Art

A system for such a use is known from WO-A1-2006/047874, which describes measurement of brain waves by use of electrodes placed in connection with at least one of the ears of a subject, i.e. placed on an outer ear part or placed in the ear canal. The measurements are used particularly for detecting the onset of an epileptic seizure. WO-A1-2006/047874 also describes the use of electrodes in pairs as detection and reference electrodes respectively, such a setup being well known in the field of electroencephalography.

U.S. Pat. No. 7,769,439 discloses an apparatus for balancing brain wave frequencies, wherein the apparatus comprises an EEG system to measure the brain left and right electrical signals and a computer for controlling the apparatus and wherein the EEG system can communicate wirelessly with the computer.

WO-A2-2007150003 discloses a system for ambulatory, long term monitoring of a physiological signal from a patient. At least part of the system may be implanted within the patient. Brain activity signals are sampled from the patient with an externally powered leadless implanted device and transmitted to a handheld patient communication device for further processing.

Generally these systems tend to be bulky, uncomfortable to wear and power consuming.

It is therefore a feature of the present invention to overcome at least these drawbacks and provide a system for bi-hemispheric brain wave measurements that is comfortable and inconspicuous to wear and that has a relatively low power consumption.

It is a further feature of the present invention to provide a method for performing bi-hemispherical brain wave measurements with a relatively low power consumption.

SUMMARY OF THE INVENTION

The invention, in a first aspect, provides a system for bi-hemispheric brain wave measurements, including a first device and a second device, wherein said first device is adapted to be worn in or at a first ear of a person subject to the measurements, and wherein said first device comprises a first and a second electrode adapted for measuring a first brain wave signal, first data acquisition means adapted for providing first digital data representing said first brain wave signal, first brain wave signal processing means configured for analyzing at least said first digital data, and first wireless link means; said second device comprises a third and a fourth electrode adapted for measuring a second brain wave signal, second data acquisition means adapted for providing second digital data representing said second brain wave signal, and second wireless link means; wherein said first and second wireless link means are adapted to establish a wireless connection between said first and said second device.

This provides a system that that is comfortable and inconspicuous to wear, whereby e.g. long term bi-hemispherical brain wave measurements can be carried out with little or no discomfort for the user.

The invention, in a second aspect, provides a method for performing bi-hemispherical brain wave measurements, a method for performing bi-hemispherical brain wave analysis, comprising the steps of providing a first device adapted for measuring a first brain wave in, or in the vicinity of, a first ear of a person subject to the analysis; providing a second device adapted for measuring a second brain wave in, or in the vicinity of, a second ear of said person; measuring said first and said second brain wave; wirelessly transmitting data representing at least one of said first and said second measured brain wave using a wireless connection between said first device and said second device; and analyzing data representing said first and said second measured brain wave, hereby providing a bi-hemispherical brain wave analysis.

This method is very well suited for long term bi-hemispherical brain wave measurements.

The invention, in a third aspect, provides a method for performing bi-hemispherical brain wave analysis, comprising the steps of providing a first device adapted for measuring a brain wave in, or in the vicinity of, a first ear of a person subject to the analysis; providing a second device adapted for providing an audio stimulation of a second ear of the person; providing a wireless connection between said first and said second device; exchanging data using said wireless connection in order to synchronize in time said first and said second device; providing an audio stimulation of said person measuring a brain wave; and analyzing said brain wave measurement with respect to the audio stimulation.

Further advantageous features appear from the dependent claims.

Still other features of the present invention will become apparent to those skilled in the art from the following description wherein the invention will be explained in greater detail.

BRIEF DESCRIPTION OF THE DRAWINGS

By way of example, there is shown and described a preferred embodiment of this invention. As will be realized, the invention is capable of other different embodiments, and its several details are capable of modification in various, obvious aspects all without departing from the invention. Accordingly, the drawings and descriptions will be regarded as illustrative in nature and not as restrictive. In the drawings.

DETAILED DESCRIPTION

Figure 1:
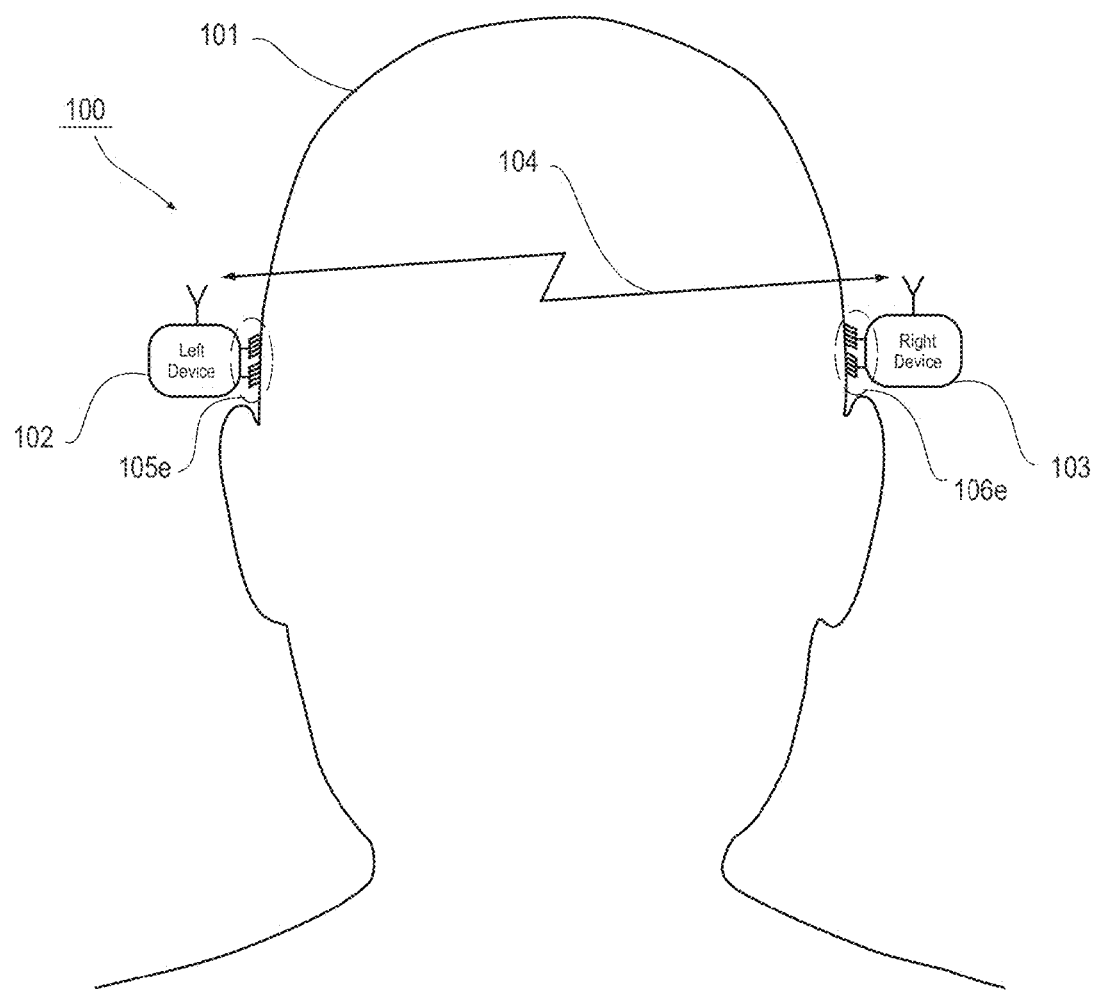
FIG. 1 illustrates highly schematically a system for bi-hemispheric brain wave measurements according to the invention.

Reference is first made to FIG. 1, which illustrates, highly schematically, a system for bi-hemispheric brain wave measurements according to the invention. The system 100 includes a first device 102 and a second device 103, and the two devices 102, 103 are adapted to be worn in or at the left ear and in or at the right ear, respectively, of the person 101 subject to the measurements (in the following also denoted the user). Each of the devices 102, 103 comprises at least a set of (i.e. two) electrodes 105e, 106e adapted for measuring a brain wave on the left side of the head and on the right side of the head.

The two devices 102, 103 are wirelessly connected through a wireless link 104 whereby a bi-hemispheric brain wave measurement can be carried out.

In a variation of the system according to FIG. 1 only one of the devices 102, 103 are worn in or at an ear of the user 101.

In yet another variation of the system according to FIG. 1, each of the devices 102, 103 includes a first part adapted to be worn at least partly within an the ear canal of the user and a second part adapted to be worn behind the ear of the user. In this variation said first part comprises at least two surface electrodes adapted to be placed in an ear canal of the user 101. This variation of the system is further described with reference to FIGS. 2 and 10.

In a variation of said embodiment, at least one of the devices 102, 103 comprises an additional electrode that is adapted to be positioned on the scalp of the user 101. This variation of the system is further described with reference to FIG. 9 and FIG. 10.

In still another variation of the system according to FIG. 1, each of the devices 102, 103 are adapted to be worn completely within an ear canal of the user 101. This system is further described with reference to FIG. 8 and FIG. 10.

In another variation of the system according to FIG. 1, each of the devices 102, 103 consists of a part, comprising a set of electrodes 105e, 106e, implanted subcutaneously outside the skull of a person wearing the system and a second part adapted to be carried behind an ear of the user 101. This system is further described with reference to FIG. 11.

Figure 2:
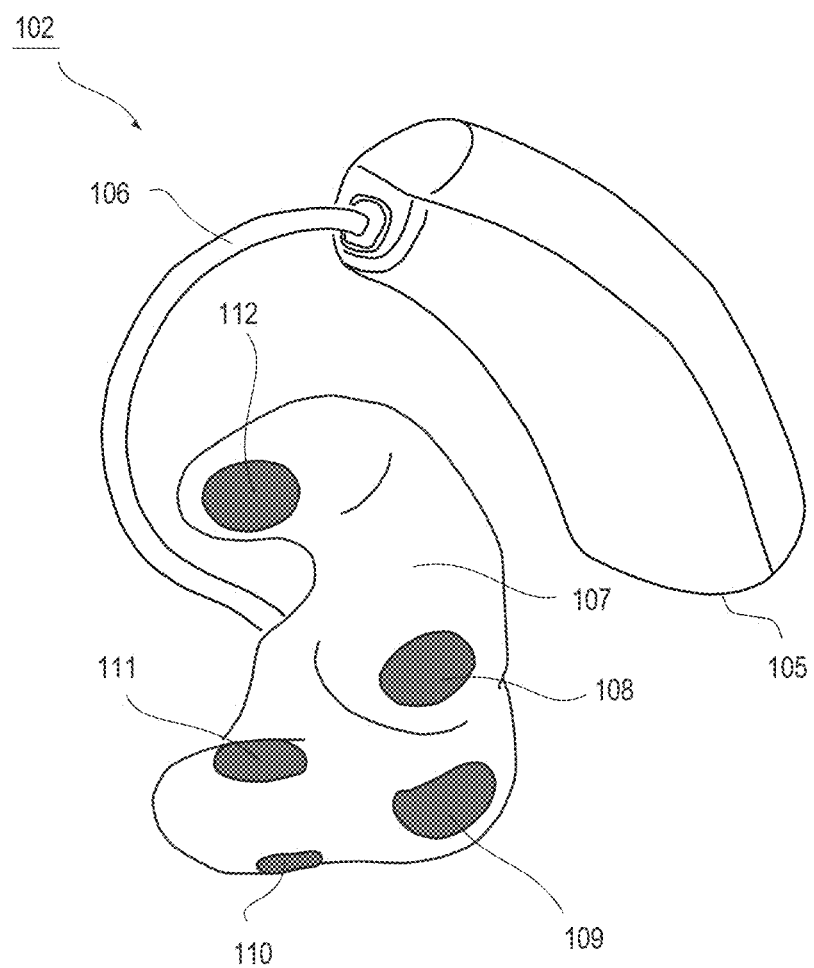
FIG. 2 illustrates highly schematically a part of a system for bi-hemispheric brain wave measurements, according to an embodiment of the invention.

Reference is now made to FIG. 2, which illustrates, in higher detail, a first device of the system for bi-hemispheric brain wave measurements, according to the an embodiment of the invention. The first device 102 comprises a housing 105, a tube 106, an earpiece 107 and electrodes 108, 109, 110, 111 and 112. The housing 105 comprises wireless link means (not shown) and an electronics module (not shown). The electronics module is adapted to process the signals received from the electrodes 108, 109, 110, 111 and 112 as will be further described below.

The tube 106 comprises electrical wires (not shown) for providing the electrode signals from the earpiece 107 and to the electronics module accommodated in the housing 105.

In a variation of the embodiment according to FIG. 2, the tube 106 is additionally adapted for guiding an acoustical signal from a speaker accommodated in the housing 105 to the earpiece 107 and further on to an ear canal of the user.

In another variation of the embodiment according to FIG. 2, a speaker is accommodated in the earpiece 107, and the tube 106 therefore comprises electrical wires configured for providing a bi-directional electrical connection. In yet another variation the bi-directional electrical connection is provided by implementing a digital data bus. Further details concerning a digital data bus can be found in e.g. WO-A1-2010/115451.

The housing 105 is adapted to be worn behind an ear of the user.

The earpiece 107 is custom molded to fit within an ear canal of the user. When inserted in the ear canal of the user, the surface of the earpiece 107 will lie adjacent to and in physical contact with the tissue of the ear of the user. The five electrodes 108, 109, 110, 111 and 112 are adapted for detecting electrical signals such as brain waves. The actual detection that will be described in detail below is preferably performed with respect to a reference point. The electrodes 108-112 are arranged on the surface of the earpiece 107. Alternatively the electrodes 108-112 may be embedded in the surface of the earpiece 107, or be arranged on or imbedded in the surface of another part of the bi-hemispheric brain wave system as will be further described below. The exact number of electrodes 108-112 provided may be more or less than the five electrodes 108-112 shown, and remains uncritical. However, the provision of at least two electrodes is preferred, as such a configuration provides for the possibility of allowing at least one of the electrodes to act as reference point, thus being a reference electrode, for the remaining electrodes, thus being detecting electrodes. Alternatively the electrodes 108-112 may be set up to operate in clusters, e.g. in pairs, with one electrode acting as a reference electrode for one or more other electrodes, thus acting as detecting electrode(s). The electrodes 108-112 are made of silver, as silver is known to have properties providing for good resistance to the harsh environment present in the human ear canal. However, any material suitable for resisting the environment in the ear canal of a human may be used.

In order to further improve the quality of the signals detected by means of the electrodes 108-112, the bi-hemispheric brain wave system may comprise a conductive gel (not shown) in connection with the electrodes 108-112.

There are numerous advantages by positioning the electrodes in the ear of the user:
- high immunity to electrical fields, due to the fact that the ear and ear canal is a cavity in the body, and the body has a high content of conductive fluid;
- high immunity to magnetic fields compared to traditional brain wave measurement setups, due to the small areal spanned;
- low amplitude of motion artifacts due to the precise fit that can be achieved between (especially an individually fitted) earpiece and the ear canal of the user;
- small skin stretch artifacts, because skin stretching is very limited in the ear canal;
- small muscle artefacts, because there are no muscles in the ear canal, and the distance to other muscles is substantial;
- good electrical interface between electrode and skin due to the high humidity in the ear canal, whereby it becomes possible to employ dry electrodes;
- an individually fitted ear piece is easy for the user to put in place, whereby a high degree of repeatability with respect to the precision of electrode placement is achieved;
- electrodes on an ear piece are discrete compared to other surface electrode placements, whereby a cosmetically attractive system can be obtained;
- with electrodes integrated in the ear piece there are no loose wires to handle for the user, and no stress on the electrodes due to forces from the wires; and
- electrodes can easily be integrated as part of the process of manufacturing of an individually fitted ear piece.

All together these advantages make in-the-ear electrodes an attractive technology, especially for long term brain wave measurements.

Long term measurements of brain wave-signals can be used for various health monitoring purposes such as e.g.:
- monitoring the users brain wave for evaluation of the result of a medical treatment;
- monitoring the user's brain wave for detection of medical states, and possibly alerting the user, caretakers or relatives. Examples of such medical states are e.g. impending hypoglycemia and epileptical seizures;
- monitoring the user's brain waves for the purpose of diagnosing diseases. Examples of such diseases are epileptic diseases as absence epilepsy, neurodegenerative diseases as Parkinsons disease and psychiatric disorders such as Schizophrenia or Anxiety disorders;
- Audio Feedback for the purpose of treating a disease or a disorder such as Attention Deficit Hyperactivity Disorder (ADHD), tinnitus or phantom pain sensations;
- Brain Computer Interface or Man-Machine Interface for the enabling the user to control the device it-self or for controlling peripheral devices.

In a variation of the embodiment according to FIG. 1, the housing 105e further comprises a speaker, the use of which will be further described below.

Figure 3:
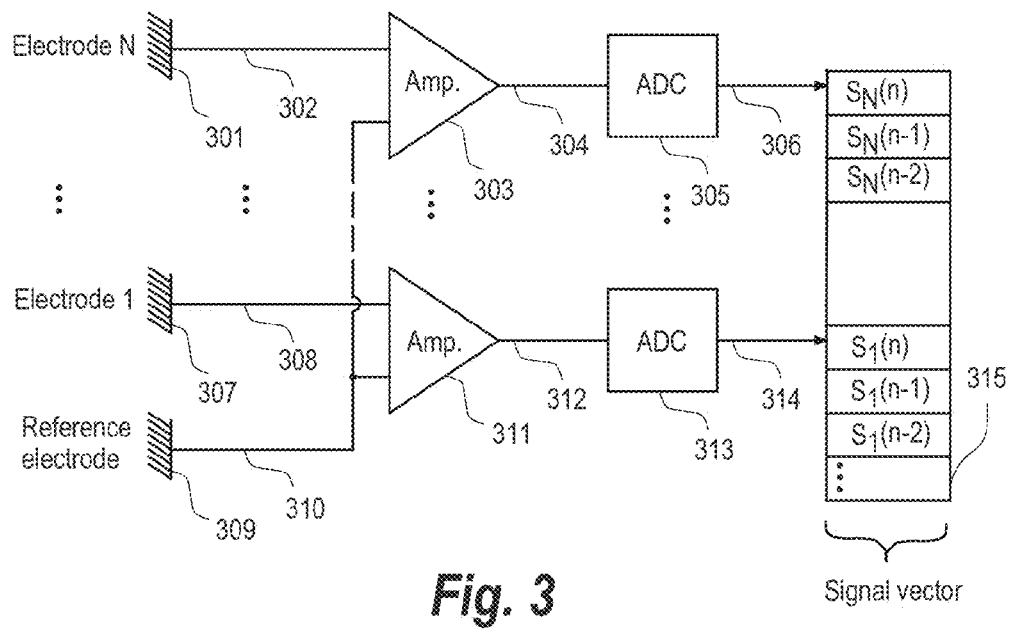
FIG. 3 illustrates highly schematically an embodiment of the initial part of the signal processing path known as the "data acquisition" according to an embodiment of the invention.

Reference is now made to FIG. 3, which illustrates, highly schematically, an embodiment of the initial part of the signal processing path known as the "data acquisition" according to an embodiment of the invention. This initial part of the electronics is known as the data acquisition part or the analog front-end. The analog front-end as shown is connected to a plurality of electrodes (electrodes 1 to N), of which FIG. 3 for the sake of simplicity shows only the first electrode 301 and the Nth electrode 307, from which input signals are received. The electrodes 301 and 307 are by means of electrical wires 302 and 308 each connected to a differential amplifier 303 and 311, respectively, for receiving and amplifying the signal detected by the electrodes 301 and 307. Each of the differential amplifiers 303 and 311 also receives input from a reference electrode 309 by means of electrical wire 310. The differential amplifiers 303 and 311 are connected to a respective analog digital converter (ADC), 305 and 313.

The ADC's 305, 313 sample the respective amplified signals, 304, 312 received from the differential amplifiers 303, 311, thereby creating output signals, 306 and 314, being discrete in time. The output signals 306, 314 from each ADC 305, 313 in combination constitute a signal vector 315 that may be written as $s=s_i(n)$, i denoting the origin of signal being sampled, i.e. electrode number i, and n denoting the sampling time. Thereby the signal vector 315 may be regarded as a signal in time and space, or as a time dependent vector. The signal vector 315 serves as input for the subsequent signal processing in the bi-hemispheric brain wave system, as will be explained below.

Brain wave signals (bio-electrical potentials) are measured differentially between two electrodes. The two devices placed on each side of the users head are connected through a wireless link, thus there is no galvanic connection. Therefore it is not possible to measure signal differentials between an electrode on the one side of the head and the other side of the head.

A signal feature may therefore be derived from a signal measured on one side, referred to as unilateral signal features, or from a combination of signals measured on one side and the other side, referred to as bilateral signal features. The signal processing advantage of the bi-hemispheric brain wave system comes from either bilateral signal features, from combinations of unilateral signal features from both side, or from using both bilateral signal features and combinations of unilateral signal features, which is more than the trivial redundancy advantage, though the robustness obtained by redundancy may also justify a bi-hemispheric brain wave system.

A vast number of signal features are of interest when processing brain wave signals, e.g. features derived using time-frequency analysis, time domain analysis and data-driven signal decomposition.

Time-frequency analysis is a body of techniques including: short time Fourier transforms, power spectrum estimations, AR-modeling, wavelet transforms, higher order spectra estimations, modified Wigner distribution functions, and Gabor-Wigner distribution functions.

Time domain analysis may be based on the broad band signal or sub-band signals obtained from a bank of band pass filters. Time domain analysis is a body of techniques including but not limited to: auto-correlation function, cross-correlation function, averaging of functions of signals, and empirical estimators of signals.

Averaging of functions of signals could for instance be an autoregressive filtering of the absolute value of the sub-band signals from a filter bank, or auto-regressive filtering of the squared value of the sub-band signals from a filter bank.

Empirical estimators of signals could for instance be percentile estimators of the sub-band signals from a filter bank, a median estimator, or a peak-to-peak time estimator.

Data-driven signal decomposition is a body of methods including but not limited to: Empirical Mode Decomposition (EMD), Hilbert-Huang spectrum, Bivariate EMD, and Complex EMD.

As described above the advantage of the bi-hemispheric signal processing system comes from either bilateral signal features, from combinations of unilateral signal features from both sides, or from using both bilateral signal features and combinations of unilateral signal features.

Generally signal features may be combined in many ways such as e.g.:
difference or ratio between two unilateral features from each side;
correlation or coherence between two unilateral features from each side, where e.g. the cross-correlation between two features may be temporal or spatial; and
more advanced statistical combinations as higher order moments, e.g. $E(x_1^2 x_2)$, or conditional expectations, e.g. $E(x_1|x_2)$;

In most of the applications of the bi-hemispheric brain wave system the electronics module comprises a Feature Extraction block and a Classifier block. These blocks are shown in the block diagrams in FIG. 4-7, that will be further described in the following.

The classifier can be a linear classifier or a non-linear classifier. Non-linear classifiers can be selected from a group comprising: Support Vector Machine (SVM), Artificial Neural Networks, Bayesian Networks, and Kernel Estimators. Additionally Hidden Markov models (HMM) may be used, and in this case it is more a sequence labeling rather than a classification.

Prior to the classifier there may be a preprocessing step for the purpose of reducing the dimensionality of the feature space. Examples of such preprocessing steps are: Principal Component Analysis (PCA), Singular Value Decomposition (SVD), Independent Component Analysis (ICA) and Non-negative Matrix Factorization (NMF).

The bi-hemispheric brain wave system comprises a left and a right device. Each of these devices comprises means for measuring brain wave signals, means for processing signals, and means for transmitting information to the contra-lateral device.

Figure 5:
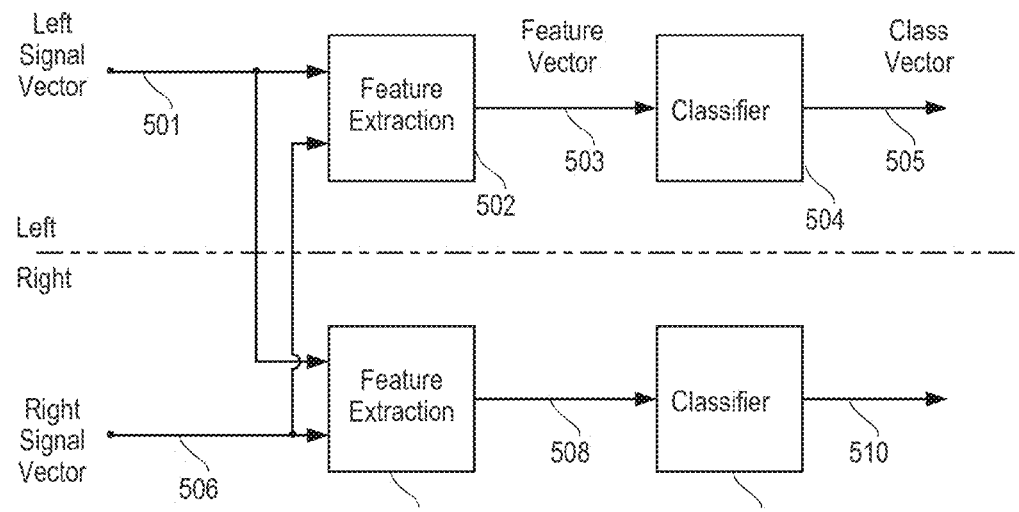
FIG. 5 shows a block diagram illustrating the feature extraction and classification process in a system for brain wave measurements according to an embodiment of the invention.
Figure 6:
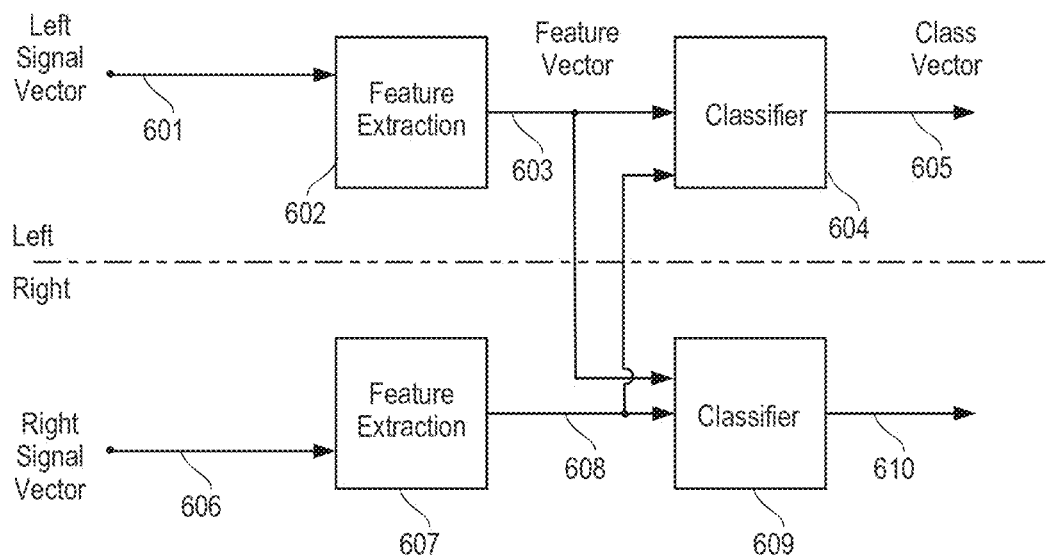
FIG. 6 shows a block diagram illustrating the feature extraction and classification process in the system for brain wave measurements according to an embodiment of the invention.
Figure 7:
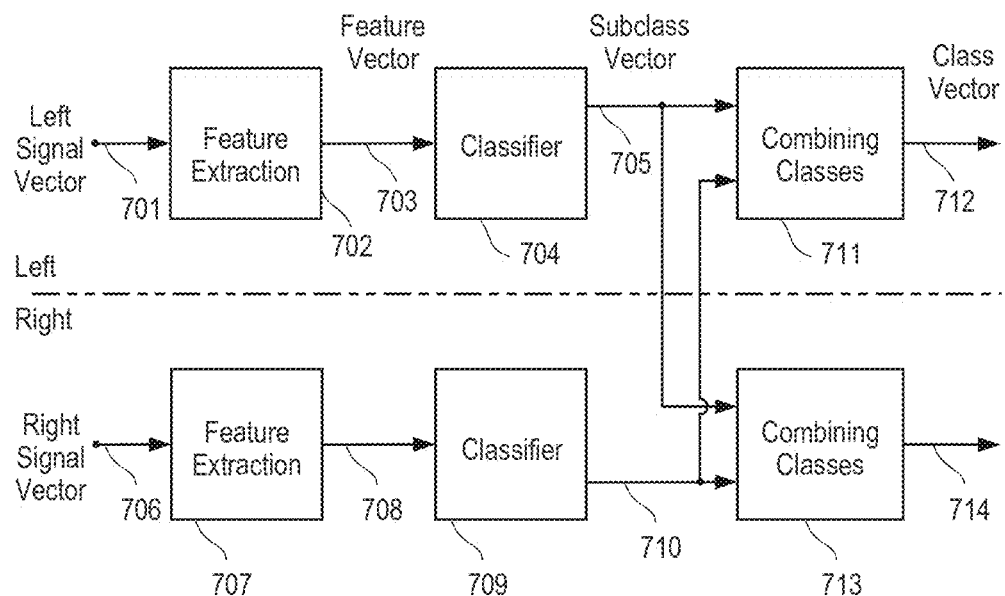
FIG. 7 shows a block diagram illustrating the feature extraction and classification process in the system for brain wave measurements according to an embodiment of the invention.

In FIGS. 5-7 are shown block diagrams illustrating the general principle of the feature extraction and classification process in a system for brain wave measurements according to an embodiment of the invention. As it appears from these diagrams the information exchange between the left and right signal processing system may appear on different levels in the signal processing. The block diagram in FIG. 5 shows a bi-hemispheric signal processing system with information exchange on a signal waveform level. The block diagram in FIG. 6 shows a bi-hemispheric signal processing system with information exchange on a signal feature level. The block diagram in FIG. 7 shows a bi-hemispheric signal processing system with information exchange on a subclass level. The information exchange may also be a combination of the sketched methods.

In variations of the examples according to FIGS. 5-7 the signal processing succeeding the information exchange level may be performed on only one side. In such case the output of the classifiers or feature extractors may also be transmitted from the device comprising the higher level signal processing to the device without this higher level signal processing.

Figure 4:
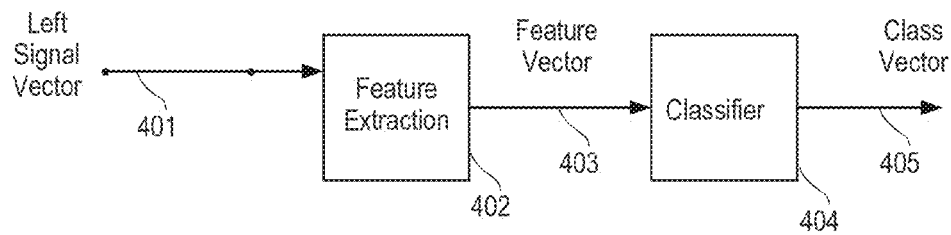
FIG. 4 shows a block diagram illustrating the general principle of the feature extraction and classification process in a system for brain wave measurements according to an embodiment of the invention.

Turning to FIG. 4 the principle of the feature extraction and feature classification process in a bi-hemispheric brain wave system according to the invention is illustrated. The signal vector 401 (315 in FIG. 3) is used as input for a feature extraction means 402. The output from the feature extraction means 402 is one or more extracted features, herein termed as "feature vector" 403, which serves as input for a classifying means 404 classifying the extracted features of the feature vector 403. In the following the output of the classifying means 404 will be termed "class vector" 405. The class vector 405 is transmitted as an output to be used in further signal processing means of the system.

To further clarify the functionality of the feature extraction means 402 and the classifying means 404, one may consider the feature extraction, f, and the classification, c, as dimension reducing mappings of the space S of signal vectors 401, the signal vector 401 being of high dimension:

$$f:S \to F \text{ and } c:F \to C$$

where F is the space of feature vectors 403 of a lower dimension and C is the set of classes of yet lower dimension constituting the class vector 405. It is likely to be expected that the feature extraction, f, and the classification, c, will have to be trained to adapt to the individual user.

Reference is now made to FIG. 5 which shows a block diagram illustrating the general principle of the feature extraction and classification process in a system for brain wave measurements according to an embodiment of the invention. The system for bi-hemispheric brain wave measurements comprises a first, e.g. left, device illustrated above the dashed line in FIG. 5 and a second, e.g. right, device illustrated below the dashed line in FIG. 5. The first and second device are both devices embodying the invention and substantially as described above with reference to FIGS. 1 and 2. In the embodiment shown, in each of the left and right devices, an analog front-end substantially as described above generates a left signal vector 501 and a right signal vector 506, respectively. In each of the left and right devices the respective signal vector 501 and 506 is used as input for a feature extraction and classification process of the type described in connection with FIG. 4. Thus, the respective signal vectors 501 and 506 are used as input for a feature extraction means 502 and 507, respectively, creating feature vectors 503 and 508, respectively, which are in turn used as input for a classification means 504 and 509, respectively, creating a class vector 505 and 510, respectively.

Furthermore, the feature extraction means 502 and 507 are by means of a transmitting means (shown as arrows on FIG. 5) interconnected for exchange of signal vectors 501 and 506. The transmitting means is a wireless transmitting means, preferably adapted for two-way communication between the devices, but may in principle be any suitable transmitting means. Such a bi-hemispheric brain wave system allows for instance for collecting a larger quantity of signals, thus providing a larger quantity of information to the signal processing device performing the final signal processing.

The transmitting means may in principle form a connection between the devices connecting other components than the above mentioned. For instance, and as illustrated in FIG. 6 featuring a variation of the embodiment according to FIG. 5, the interconnection may be provided between the classifying means 604 and 609, respectively, of the devices, thus enabling exchange of feature vectors 603 and 608, respectively, between the devices. The signal vectors 601 and 606, feature extraction means 602 and 607 and feature vectors 603 and 608 correspond to the signal vectors 501 and 506, feature extraction means 502 and 507 and feature vectors 503 and 508 described with reference to FIG. 5. The feature vectors 603 and 608 are used as input for the classification means 604 and 609, creating respection class vectors 605 and 610.

As illustrated in FIG. 7 featuring an embodiment of the process shown in FIG. 5, another possibility is to provide an interconnection for exchanging the output of the respective classification means 704 and 709, in FIG. 7 called subclass vectors 705 and 710. In this case, each device of the bi-hemispheric brain wave system further comprises class combining means 711 and 713, respectively, for combining the subclass vectors 705 and 710, respectively, to form the final class vectors 712 and 714, respectively. The signal vectors 701 and 706, feature extraction means 702 and 707 and feature vectors 703 and 708 correspond to the signal vectors 501 and 506, feature extraction means 502 and 507 and feature vectors 503 and 508 described with reference to FIG. 5.

Figure 8:
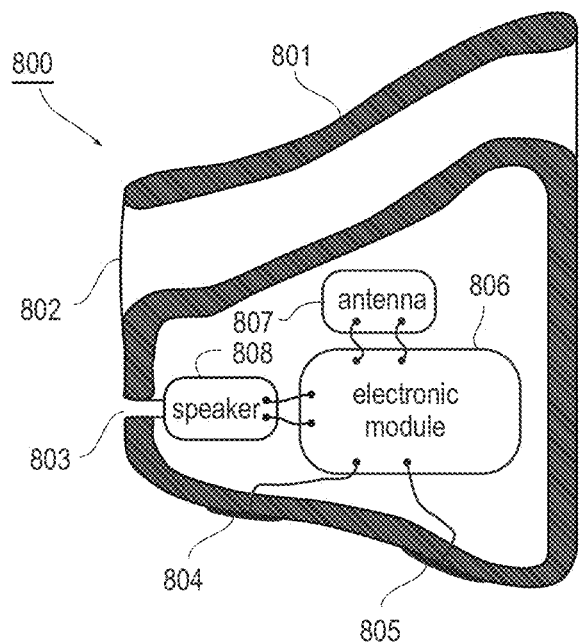
FIG. 8 illustrates highly schematically a cross-section of a part of a system for bi-hemispheric brain wave measurements according to an embodiment of the invention.

Reference is now made to FIG. 8, which illustrates, highly schematically, a cross-section of a part of a system for bi-hemispheric brain wave measurements, according to an embodiment of the invention. The device 800 comprises a housing 801, a through going conduit 802, a sound passage 803 through said housing 801, electrodes 804 and 805, an electronics module 806, an antenna 807 and a speaker 808. The figure also shows electrical wires connecting the electrodes 804, 805, the antenna 807 and the speaker 808 with the electronics module 806.

This device is advantageous in that it is possible to position the device completely within an ear canal of a user, while still being able to maintain a wireless link with other devices, such as e.g. the contra-lateral device of the bi-hemispheric brain wave system. The housing has a through going conduit or vent 802 for the purpose of avoiding acoustical occlusion of the user's ear-canal when the device is inserted.

The housing 801 is molded as a custom made shell that has been manufactured based on an impression of the ear canal of the user, whereby an individually fitted device is obtained. The electrodes 804, 805 are embedded on the outer surface of the housing 801. The speaker 808 and the sound passage 803 are configured to allow an audio input to be provided to the user of the device. The antenna 807 constitutes together with the electronics module 806 the wireless link means required to maintain a wireless connection with other wireless devices.

In a variation of the embodiment according to FIG. 8, the through going conduit 802 is omitted. Hereby the device may function as an earplug, in case the user so desires, due to the significant acoustical attenuation provided by such a device. In a further variation hereof such a device may include a microphone whereby the user can achieve normal or even improved hearing capabilities (through advanced signal processing in the electronics module 806, such as e.g. speech enhancing algorithms) despite the acoustical attenuation provided by the device.

In another variation of the embodiment according to FIG. 8, the speaker 808 is used for delivering a message to the user of the device based on the analysis of the bi-hemispheric brain wave measurements. In yet another variation the speaker 808 is used for delivering an auditory treatment signal to the user of the device based on the analysis of the bi-hemispheric brain wave measurements. In still another variation the speaker 808 is used for stimulating a brain wave response. One such brain wave response is an auditory evoked brainstem response. In further variations the speaker is omitted in one or both of the devices of the system according to the invention, and generally it is true for all disclosed embodiments that the speaker is only optional.

This device is especially advantageous for use in sleep monitoring because the positioning of the device inside the ear canal of the user allows the user to sleep without any restrictions with respect to how the user positions himself or herself during sleep. As an example a system with a behind-the-ear device may be uncomfortable if the user prefers to sleep on the side, and with a traditional sleep monitoring system with wired electrode pads fixed in numerous positions on the user's head it will hardly be possible to move at all during sleep.

In yet another variation of the embodiment according to FIG. 8, the wireless link means 806, 807 are connected to an external device such as a remote server, whereby sleep monitoring can be carried out while the user sleeps at home.

Figure 9:
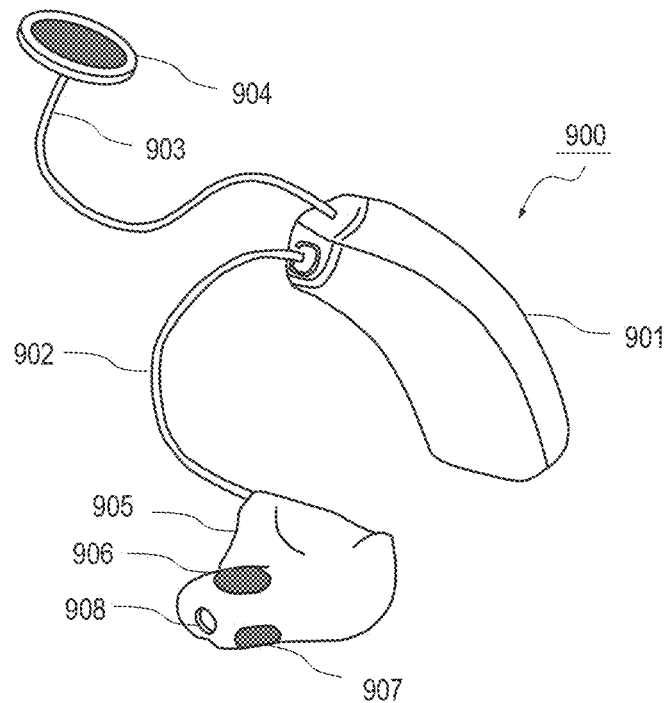
FIG. 9 illustrates highly schematically a part of a system for bi-hemispheric brain wave measurements according to an embodiment of the invention.

Reference is now made to FIG. 9, which illustrates, highly schematically, a part of a system for bi-hemispheric brain wave measurements, according to an embodiment of the invention. The device 900 comprises a housing 901, tubes 902 and 903, an earpiece 905, electrodes 904, 906, and 907 and a through going conduit 908. The housing 901 comprises wireless link means (not shown) and an electronics module (not shown). The electronics module is adapted to process the signals received from the electrodes 904, 906 and 907 through the corresponding electrical wires held in the tubes 902 and 903.

The electrode 904 is a pad electrode that can be positioned anywhere on the user's body whereby the versatility of the system may be even further improved.

In a variation of the embodiment according to FIG. 9, the pad electrode 904 and the tube 903 is detachably connected to the housing 901. According to the embodiment of FIG. 9 the housing 901 is adapted to be worn behind the ear, but in a variation the detachable pad electrode 904 and tube 903 may as well be detachably connected to a housing such as the housing 801 described with reference to the embodiment according to FIG. 8.

Several variations exist with regard to the tube 902, whereof several have been described with reference to FIG. 2.

Generally all the embodiments of the system according to the invention are especially advantageous for use in methods of treatment that provide an auditory signal in response to a bi-hemispheric measurement, since in this case no other system devices or components are required for carrying out the method because the two electronics modules accommodated in each of the two devices calculate the required auditory signals based on the bi-hemispheric measurements and two speakers likewise accommodated in each of the two devices provide the two auditory signals.

One example of such a method is described in U.S. Pat. No. 7,769,439, which discloses a method for balancing brain wave frequencies, wherein a binaural beat is provided to the person being treated, wherein the frequency range of the binaural beat is determined by measured bi-hemispheric signals.

Generally all the embodiments of the system according to the invention are also especially advantageous for use in methods of treatment or diagnosis that comprise contra-lateral auditory stimulation in connection with brain wave measurements, such as e.g. Auditory Brainstem Response (ABR), because the system according to the invention allows the (contra-lateral) stimuli and the brain wave measurements to be coordinated.

One example of such a method is described in "Ipsilateral and Contralateral Acoustic Brainstem Response Abnormalities in Patients With Vestibular Schwannoma" in Otolaryngol Head Neck Surg Dec. 1, 2009 vol. 141 no. 6 695-70, by Chien Shih, et al., which discloses a method for early diagnosis of brain tumors, based on contra-laterally evoked brainstem responses.

Generally auditory evoked ABR measurements can be carried out during sleep, because the auditory stimuli can be so weak that a patient will typically not wake up due to the auditory stimuli.

Generally all the embodiments of the system according to the invention are especially advantageous for use in methods of treatment that require a binaural auditory stimulation in response to a brain wave measurement, because the wireless connection allows the auditory stimulation in the left ear and in the right ear to be synchronized in time whereby a binaural auditory stimulation can be provided.

Figure 10:
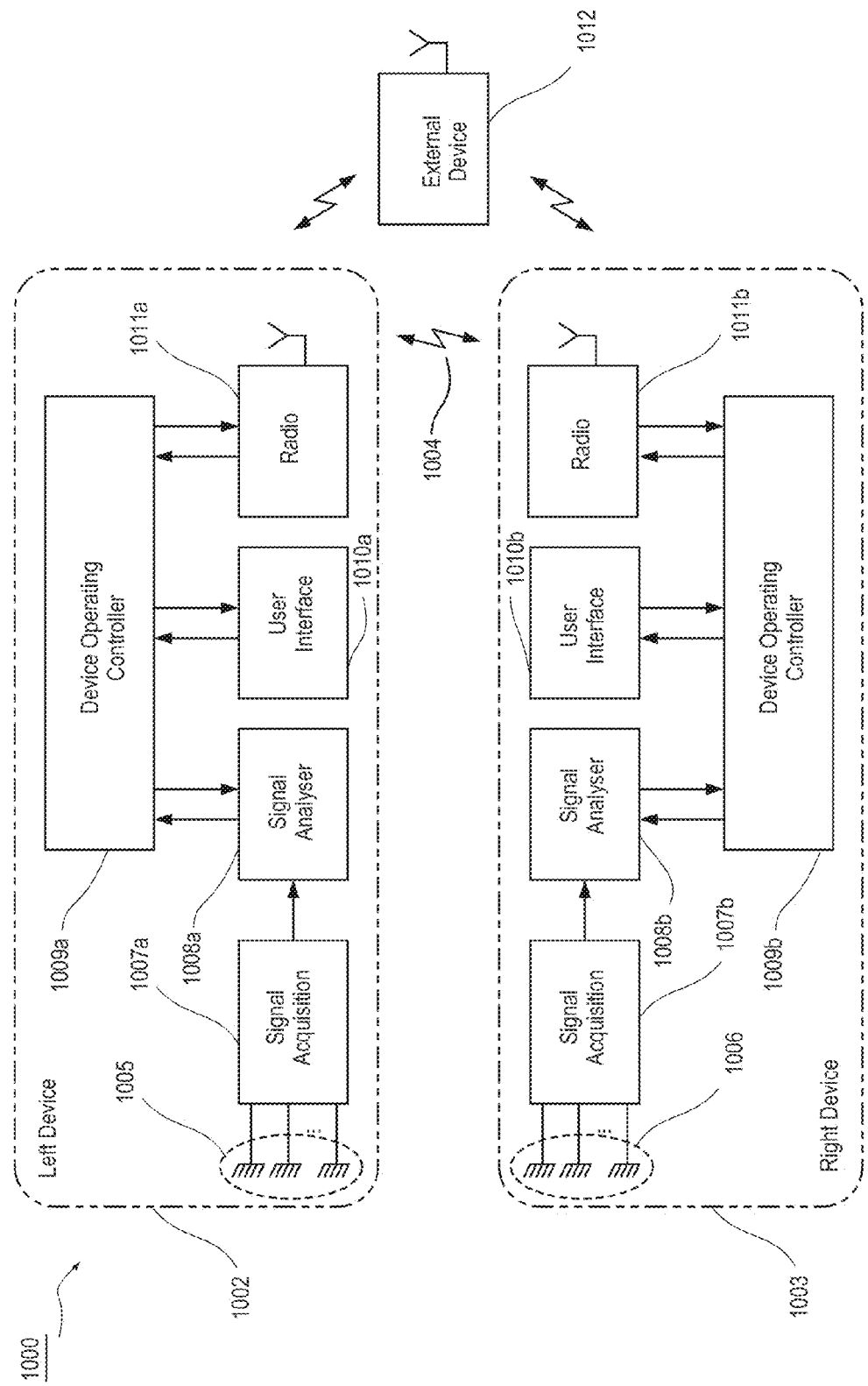
FIG. 10 illustrates highly schematically a block diagram of a system for bi-hemispheric brain wave measurements according to an embodiment of the invention.

Reference is made to FIG. 10, which illustrates a block diagram of a system for bi-hemispheric brain wave measurements, according to an embodiment of the invention. The basic functionality of this block diagram is common for all the device embodiments described above with reference to FIGS. 2, 8 and 9.

The system 1000 comprises a left device 1002 and a right device 1003. The two devices 1002, 1003 comprise the same elements in the block diagram, namely: a set of electrodes 1005, 1006 adapted for measuring brain wave signals, data acquisition means 1007a-b adapted for providing digital data representing said measured brain wave signals, brain wave signal processing means 1008a-b adapted for processing the digital data provided by the data acquisition means 1007a-b, user interface 1010a-b adapted for allowing the user of the system to interact with the system, wireless link means 1011a-b adapted for establishing a wireless connection 1004 between said left device and said right device and device controller 1009a-b configured to control the operation of the devices 1002, 1003. Further, at least one of the wireless link means 1011a-b is adapted for establishing a wireless connection with an external device 1012. Hereby the result of the brain wave analysis or just the digital data representing the brain wave measurements can be transmitted to the external device 1012. In this way the external device 1012 can be used for alerting purposes or for carrying out at least part of the brain wave analysis.

In a variation according to the embodiment of FIG. 10, the wireless link means 1011a-b are not adapted for establishing a wireless connection with an external device 1012.

Generally all the disclosed embodiments can in a variation comprise wireless link means adapted for establishing a wireless connection with an external device.

Figure 11:
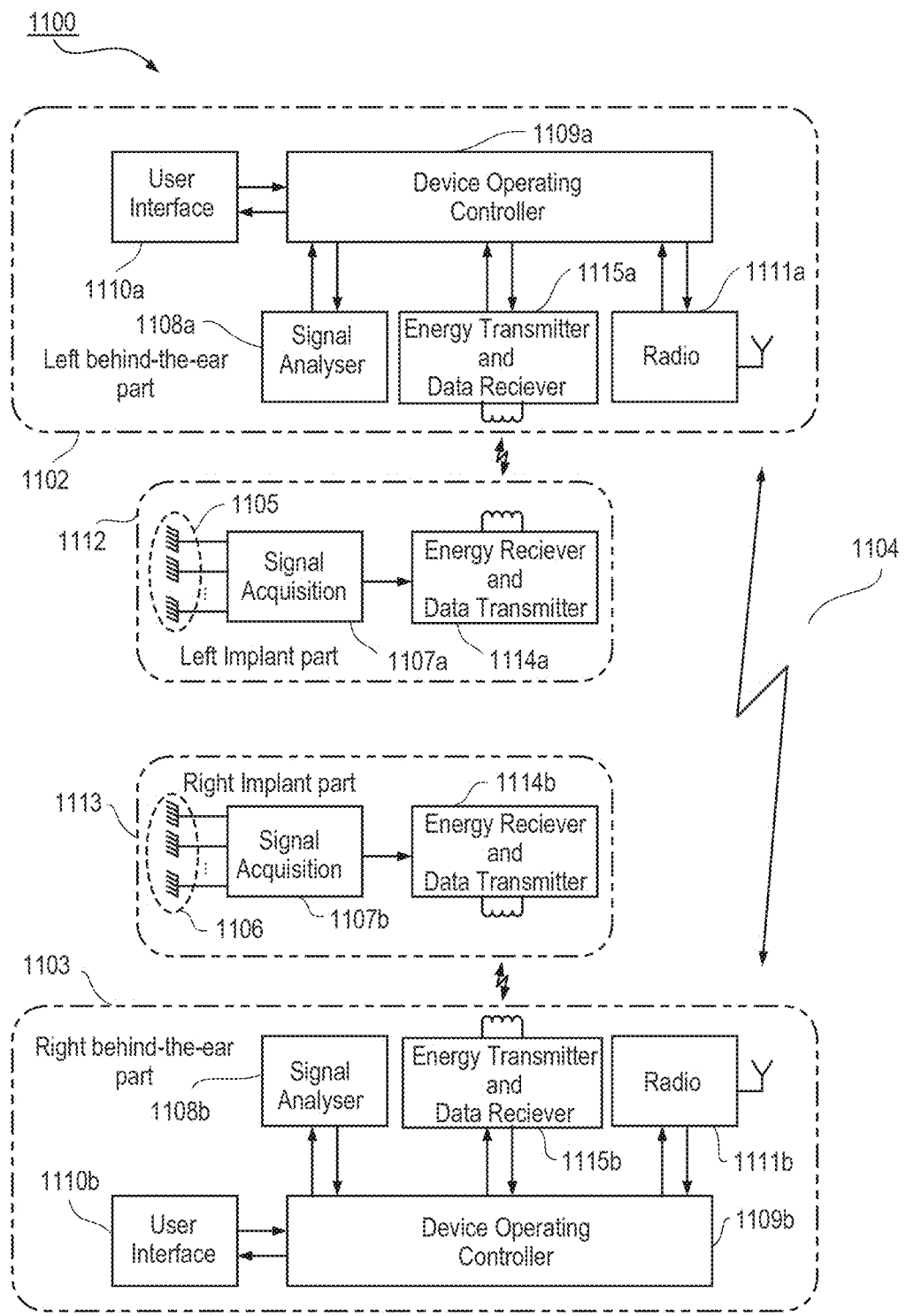
FIG. 11 illustrates highly schematically a block diagram of a system for bi-hemispheric brain wave measurements according to an embodiment of the invention.

Reference is now made to FIG. 11, which illustrates a block diagram of a system for bi-hemispheric brain wave measurements, according to an embodiment of the invention. In the system 1100 according to this embodiment the left and right devices each comprises a first part 1112, 1113 adapted to be implanted subcutaneously outside the skull of a person wearing the system and a second part 1102, 1103 adapted to be carried behind the ear of said person.

The system 1100 comprises the elements already described with reference to FIG. 10 namely: a set of electrodes 1105, 1106 adapted for measuring brain wave signals, data acquisition means 1107a-b adapted for providing digital data representing said measured brain wave signals, brain wave signal processing means 1108a-b adapted for processing the digital data provided by the data acquisition means 1107a-b, user interface 1110a-b adapted for allowing the user of the system to interact with the system, device controller 1109a-b configured to control the operation of the left behind-the-ear part 1102 and the right behind-the-ear part 1103, respectively, and wireless link means 1111a-b adapted for establishing a wireless connection 1104 between said left behind-the-ear part 1102 and said right behind-the-ear part 1103.

In this system 1100, the electrodes 1105, 1106 and data acquisition means 1107a-b are accommodated in the respective implanted parts 1112, 1113, together with wireless means 1114a-b that are configured such that digital data are transmitted from the implanted parts 1112, 1113 and to the wireless parts 1115a-b in the corresponding behind-the-ear parts 1102, 1103, and energy to power the implanted parts 1112, 1113 are transmitted from the behind-the-ear parts 1102, 1103 and to the corresponding implanted parts 1112, 1113.

In a further variation of the embodiment according to FIG. 11, the wireless link means 1114a-b are implemented as described in patent application PCT/EP2010/054534, filed on 6 Apr. 2010 with the European Patent Office, and published as WO-A1-2011124251.

In a variation according to all the disclosed embodiments the wireless connection between the left and right device is implemented by the use of an inductive short range radio, that has a very low power consumption.

Other modifications and variations of the structures and procedures will be evident to those skilled in the art.

We claim:

1. A system for bi-hemispheric brain wave measurements, comprising:

a first device configured to be worn in or at a first ear of a person subject to the measurements and comprising a first and a second measurement electrode adapted for measuring a first brain wave signal, a first data acquisition component coupled to said measurement electrodes, said first data acquisition component comprising at least one amplifier and configured to provide first digital data representing said first brain wave signal, a first brain wave signal analyzer configured for analyzing at least said first digital data, and first wireless link component operable to establish a wireless connection with a second wireless link component; and a second device configured to be worn in or at a second ear of said person and comprising a third and a fourth measurement electrode adapted for measuring a second brain wave signal, a second data acquisition component coupled to said measurement electrodes, said second data acquisition component comprising at least one amplifier and configured to provide second digital data representing said second brain wave signal, and said second wireless link component;

wherein said first brain wave signal analyzer is configured to combine a first characteristic feature and second characteristic feature during the course of its analysis, wherein the first characteristic feature is derived unilaterally from the first device of the system and the second characteristic feature is derived unilaterally from the second device of the system, wherein the system is configured for detection of at least one of impending hypoglycemia or epileptic seizures based said analysis by said first brain wave signal analyzer, and redundancy from having a combination of unilateral signal features is provided to improve robustness of said system.

2. The system according to claim 1, wherein at least one of said first and said second device of said system comprises a first part implanted subcutaneously outside the skull of said person and a second part adapted to be carried behind the ear of said person, wherein said first part comprises the measurement electrodes of at least one of said first and said second device.

3. The system according to claim 2, wherein said second part includes said first wireless link component as well as a further wireless link component configured to establish a wireless link between said first and second parts.

4. The system according to claim 3, wherein each of said first and second devices includes a further wireless link component for establishing a wireless connection with an external device.

5. The system according to claim 1, wherein at least one of said first and said second device of said system is adapted to be worn at least partly within an ear canal of said person, and wherein the measurement electrodes of at least one of said first and said second device comprise at least two surface electrodes adapted to be placed in said ear canal.

6. The system according to claim 5, wherein at least one of said first and said second device of said system comprises a shell, wherein the contours of the outer surface of said shell and said measurement electrodes are individually matched to at least part of said ear canal.

7. The system according to claim 6, wherein each of said first and second devices is configured to be positioned completely within a respective ear of said person, each of said first and second devices comprising a shell having outer surface contours individually matched to at least part of the respective ear canal, with contact surfaces of said measurement electrodes also individually matched to said part of said respective ear canal.

8. The system according to claim 1, comprising a fifth electrode adapted for attachment to the scalp of said person, hereby providing a third brain wave signal.

9. The system according to claim 8 comprising a connector for providing a detachable connection between said fifth electrode and said first or said second device of the system.

10. The system according to claim 1, wherein said first brain wave signal analyzer is configured to derive a characteristic feature of a brain wave signal based on an analysis method selected from a group consisting of time-frequency analysis, time-domain analysis and data-driven signal decomposition.

11. The system according to claim 10, wherein said first brain wave signal analyzer is configured to combine a first brain wave signal from the first device with a second brain wave signal from the second device and to derive a characteristic feature based on the two signals, whereby a bilateral signal feature is provided.

12. The system according to claim 1, wherein said first brain wave signal analyzer is configured to combine a first characteristic feature and a second characteristic feature, using a method selected from a group consisting of difference, ratio, correlation, coherence, higher order moments and conditional expectations.

13. The system according to claim 1, wherein said system comprises a first speaker, and wherein said wireless connection provides co-ordination between said first and said second device such that a brain wave measurement can be performed based on a contra-lateral auditory stimulation by said first speaker.

14. The system according to claim 13, wherein said brain wave measurement provides a measurement of an auditory brainstem response.

15. The system according to claim 13, wherein said first speaker is accommodated in said first device, and a second speaker is accommodated in said second device, wherein said first device is adapted to provide a first auditory signal that is frequency shifted relative to a second auditory signal provided by said second device, whereby a binaural beat is provided to the user.

16. The system according to claim 1, wherein each of said first and second devices is configured to be positioned completely within a respective ear canal of said person.

17. The system according to claim 1, wherein each of said first and second devices includes a further wireless link component for establishing a wireless connection with an external device.

18. The system according to claim 1, wherein the second device includes a second brain wave signal analyzer that is configured in the same way as the first brain wave signal analyzer.

19. The system according to claim 1, wherein said first brain wave signal analyzer includes:
a feature extractor for extracting features from said first digital data and from said second digital data, including said first and second characteristic features; and
a classifier responsive to the extracted features and generating a class vector representing a classification of said extracted features.

20. A method for performing bi-hemispherical brain wave analysis, comprising the steps of:
measuring a first brain wave at a first device in, or in the vicinity of, a first ear of a person subject to the analysis;
measuring a second brain wave at a second device in, or in the vicinity of, a second ear of said person;
wirelessly transmitting data representing at least one of said first and said second measured brain wave using a wireless connection between said first device and said second device; and
analyzing data representing said first and said second measured brain wave, hereby providing a bi-hemispherical brain wave analysis;
wherein said analyzing step comprises combining a first characteristic feature and second characteristic feature, wherein the first characteristic feature is derived unilaterally from the first device and the second characteristic feature is derived unilaterally from the second device, wherein the method comprises detection of at least one of impending hypoglycemia or epileptic seizures based on results of said analyzing, and redundancy from having a combination of unilateral signal features is provided to improve robustness of said method.

21. The method according to claim 20, comprising the steps of providing a first audio stimulation of the first ear of said person, providing a second audio stimulation of the second ear of said person, and synchronizing in time said first and second audio stimulation hereby providing binaural audio stimulation.

22. The method according to claim 20, wherein the brain wave analysis is conducted by a signal processor located within one of said first and second devices.

23. A method for performing bi-hemispherical brain wave analysis, comprising the steps of:
- providing from a first device an audio stimulation of a first ear of a person subject to an analysis;
- measuring a brain wave at a second device in, or in the vicinity of, a second ear of said person;
- exchanging data over a wireless connection between said first and second devices in order to synchronize in time said first and said second device;
- analyzing said brain wave measurement with respect to the audio stimulation;
- wherein said analyzing step comprises combining a first characteristic feature and second characteristic feature, wherein the first characteristic feature is derived unilaterally from the first device and the second characteristic feature is derived unilaterally from the second device, wherein the method comprises detection of at least one of impending hypoglycemia and epileptic seizures based on said analyzing, and redundancy from having a combination of unilateral signal features is provided to improve robustness of said detection.

24. The method according to claim 23, wherein said brain wave measurement and a contra-lateral audio stimulation are synchronized in time.

25. The method according to claim 24, wherein said brain wave measurement provides an auditory evoked brainstem response.

26. The method according to claim 24, wherein said brain wave measurement provides an EEG measurement.

27. The method according to claim 23, wherein said analyzing step is conducted by a signal processor located within one of said one of said first and second devices.

* * * * *